(12) United States Patent
Heise et al.

(10) Patent No.: US 10,450,151 B2
(45) Date of Patent: Oct. 22, 2019

(54) LABORATORY SAMPLE DISTRIBUTION SYSTEM AND CORRESPONDING METHOD OF OPERATION

(71) Applicant: Roche Diagnostics Operations, Inc., Indianapolis, IN (US)

(72) Inventors: Michael Heise, Marbach (DE); Hans Schneider, Schwaikheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 368 days.

(21) Appl. No.: 15/418,830

(22) Filed: Jan. 30, 2017

(65) Prior Publication Data

US 2017/0138971 A1  May 18, 2017

Related U.S. Application Data

(63) Continuation of application No. 14/262,945, filed on Apr. 28, 2014, now Pat. No. 9,664,703, which is a continuation of application No. PCT/EP2012/071762, filed on Nov. 2, 2012.

(30) Foreign Application Priority Data

Nov. 4, 2011 (EP) .................................... 11187977

(51) Int. Cl.
  *B65G 54/02* (2006.01)
  *G01N 35/04* (2006.01)
  *G01N 35/00* (2006.01)

(52) U.S. Cl.
  CPC ............. *B65G 54/02* (2013.01); *G01N 35/04* (2013.01); *B65G 2203/045* (2013.01); *B65G 2203/046* (2013.01); *G01N 2035/00772* (2013.01); *G01N 2035/0477* (2013.01)

(58) Field of Classification Search
  None
  See application file for complete search history.

(56) References Cited

U.S. PATENT DOCUMENTS

| | | | |
|---|---|---|---|
| 3,273,727 A | 9/1966 | Rogers et al. |
| 3,653,485 A | 4/1972 | Donlon |
| 3,901,656 A | 8/1975 | Durkos et al. |
| 4,150,666 A | 4/1979 | Brush |
| 4,395,164 A | 7/1983 | Beltrop et al. |
| 4,544,068 A | 10/1985 | Cohen |

(Continued)

FOREIGN PATENT DOCUMENTS

| | | |
|---|---|---|
| CN | 201045617 Y | 4/2008 |
| CN | 102109530 A | 6/2011 |

(Continued)

*Primary Examiner* — Michael S Lowe
(74) *Attorney, Agent, or Firm* — Roche Diagnostics Operations, Inc.

(57) ABSTRACT

A laboratory sample distribution system is presented. The laboratory sample distribution system comprises a number of container carriers. The container carriers each comprise at least one magnetically active device such as, for example, at least one permanent magnet, and carry a sample container. The system further comprises a transport plane to carry the container carriers and a number of electro-magnetic actuators being stationary arranged below the transport plane. The electro-magnetic actuators move a container carrier on top of the transport plane by applying a magnetic force to the container carrier.

19 Claims, 6 Drawing Sheets

(56) References Cited

U.S. PATENT DOCUMENTS

| | | |
|---|---|---|
| 4,771,237 A | 9/1988 | Daley |
| 5,120,506 A | 6/1992 | Saito et al. |
| 5,295,570 A | 3/1994 | Grecksch et al. |
| 5,309,049 A | 5/1994 | Kawada et al. |
| 5,457,368 A | 10/1995 | Jacobsen et al. |
| 5,523,131 A | 6/1996 | Isaacs et al. |
| 5,530,345 A | 6/1996 | Murari et al. |
| 5,636,548 A | 6/1997 | Dunn et al. |
| 5,641,054 A | 6/1997 | Mori et al. |
| 5,651,941 A | 7/1997 | Stark et al. |
| 5,720,377 A | 2/1998 | Lapeus et al. |
| 5,735,387 A | 4/1998 | Polaniec et al. |
| 5,788,929 A | 8/1998 | Nesti |
| 6,045,319 A | 4/2000 | Uchida et al. |
| 6,062,398 A | 5/2000 | Thalmayr |
| 6,141,602 A | 10/2000 | Igarashi et al. |
| 6,151,535 A | 11/2000 | Ehlers |
| 6,184,596 B1 | 2/2001 | Ohzeki |
| 6,191,507 B1 | 2/2001 | Peltier et al. |
| 6,206,176 B1 | 3/2001 | Blonigan et al. |
| 6,255,614 B1 | 7/2001 | Yamakawa et al. |
| 6,260,360 B1 | 7/2001 | Wheeler |
| 6,279,728 B1 | 8/2001 | Jung et al. |
| 6,293,750 B1 | 9/2001 | Cohen et al. |
| 6,429,016 B1 | 8/2002 | McNeil |
| 6,444,171 B1 | 9/2002 | Sakazume et al. |
| 6,571,934 B1 | 6/2003 | Thompson et al. |
| 7,028,831 B2 | 4/2006 | Veiner |
| 7,078,082 B2 | 7/2006 | Adams |
| 7,122,158 B2 | 10/2006 | Itoh |
| 7,278,532 B2 | 10/2007 | Martin |
| 7,326,565 B2 | 2/2008 | Yokoi et al. |
| 7,425,305 B2 | 9/2008 | Itoh |
| 7,428,957 B2 | 9/2008 | Schaefer |
| 7,578,383 B2 | 8/2009 | Itoh |
| 7,597,187 B2 | 10/2009 | Bausenwein et al. |
| 7,850,914 B2 | 12/2010 | Veiner et al. |
| 7,858,033 B2 | 12/2010 | Itoh |
| 7,875,254 B2 | 1/2011 | Garton et al. |
| 7,939,484 B1 | 5/2011 | Loeffler et al. |
| 8,240,460 B1 | 8/2012 | Bleau et al. |
| 8,281,888 B2 | 10/2012 | Bergmann |
| 8,502,422 B2 | 8/2013 | Lykkegaard |
| 8,796,186 B2 | 8/2014 | Shirazi |
| 8,833,544 B2 | 9/2014 | Stoeckle et al. |
| 9,097,691 B2 | 8/2015 | Onizawa et al. |
| 9,187,268 B2 | 11/2015 | Denninger et al. |
| 9,211,543 B2 | 12/2015 | Ohga et al. |
| 9,239,335 B2 | 1/2016 | Heise et al. |
| 9,423,410 B2 | 8/2016 | Buehr |
| 9,423,411 B2 | 8/2016 | Riether |
| 10,126,317 B2 | 11/2018 | Heise et al. |
| 10,175,259 B2 | 1/2019 | Riether |
| 2002/0009391 A1 | 1/2002 | Marquiss et al. |
| 2003/0092185 A1 | 5/2003 | Qureshi et al. |
| 2004/0050836 A1 | 3/2004 | Nesbitt et al. |
| 2004/0084531 A1 | 5/2004 | Itoh |
| 2005/0061622 A1 | 3/2005 | Martin |
| 2005/0109580 A1 | 5/2005 | Thompson |
| 2005/0194333 A1 | 9/2005 | Veiner et al. |
| 2005/0196320 A1 | 9/2005 | Veiner et al. |
| 2005/0226770 A1 | 10/2005 | Allen et al. |
| 2005/0242963 A1 | 11/2005 | Oldham et al. |
| 2005/0247790 A1 | 11/2005 | Itoh |
| 2005/0260101 A1 | 11/2005 | Nauck et al. |
| 2005/0271555 A1 | 12/2005 | Itoh |
| 2006/0000296 A1 | 1/2006 | Salter |
| 2006/0047303 A1 | 3/2006 | Ortiz et al. |
| 2006/0219524 A1 | 10/2006 | Kelly et al. |
| 2007/0116611 A1 | 5/2007 | DeMarco |
| 2007/0210090 A1 | 9/2007 | Sixt et al. |
| 2007/0248496 A1 | 10/2007 | Bondioli et al. |
| 2007/0276558 A1 | 11/2007 | Kim |
| 2008/0012511 A1 | 1/2008 | Ono |
| 2008/0029368 A1 | 2/2008 | Komori |
| 2008/0056328 A1 | 3/2008 | Rund et al. |
| 2008/0131961 A1 | 6/2008 | Crees et al. |
| 2009/0004732 A1 | 1/2009 | LaBarre et al. |
| 2009/0022625 A1 | 1/2009 | Lee et al. |
| 2009/0081771 A1 | 3/2009 | Breidford et al. |
| 2009/0128139 A1 | 5/2009 | Drenth et al. |
| 2009/0142844 A1 | 6/2009 | Le Comte |
| 2009/0180931 A1 | 7/2009 | Silbert et al. |
| 2009/0322486 A1 | 12/2009 | Gerstel |
| 2010/0000250 A1 | 1/2010 | Sixt |
| 2010/0152895 A1 | 6/2010 | Dai |
| 2010/0175943 A1 | 7/2010 | Bergmann |
| 2010/0186618 A1 | 7/2010 | King et al. |
| 2010/0255529 A1 | 10/2010 | Cocola et al. |
| 2010/0300631 A1 | 12/2010 | Pedrazzini |
| 2010/0312379 A1 | 12/2010 | Pedrazzini |
| 2011/0050213 A1 | 3/2011 | Furukawa |
| 2011/0124038 A1 | 5/2011 | Bishop et al. |
| 2011/0172128 A1 | 7/2011 | Davies et al. |
| 2011/0186406 A1 | 8/2011 | Kraus et al. |
| 2011/0287447 A1 | 11/2011 | Norderhaug et al. |
| 2012/0037696 A1 | 2/2012 | Lavi |
| 2012/0129673 A1 | 5/2012 | Fukugaki et al. |
| 2012/0178170 A1 | 7/2012 | Van Praet |
| 2012/0211645 A1 | 8/2012 | Tullo et al. |
| 2012/0275885 A1 | 11/2012 | Furrer et al. |
| 2012/0282683 A1 | 11/2012 | Mototsu |
| 2012/0295358 A1 | 11/2012 | Ariff et al. |
| 2012/0310401 A1 | 12/2012 | Shah |
| 2013/0034410 A1 | 2/2013 | Heise et al. |
| 2013/0126302 A1 | 5/2013 | Johns et al. |
| 2013/0153677 A1 | 6/2013 | Leen et al. |
| 2013/0180824 A1 | 7/2013 | Kleinikkink et al. |
| 2013/0263622 A1 | 10/2013 | Mullen et al. |
| 2013/0322992 A1 | 12/2013 | Pedrazzini |
| 2014/0170023 A1 | 6/2014 | Saito et al. |
| 2014/0234065 A1 | 8/2014 | Heise et al. |
| 2014/0234949 A1 | 8/2014 | Wasson et al. |
| 2015/0014125 A1 | 1/2015 | Hecht |
| 2015/0166265 A1 | 6/2015 | Pollack et al. |
| 2015/0241457 A1 | 8/2015 | Miller |
| 2015/0273468 A1 | 10/2015 | Croquette et al. |
| 2015/0273691 A1 | 10/2015 | Pollack |
| 2015/0276775 A1 | 10/2015 | Mellars et al. |
| 2015/0276776 A1 | 10/2015 | Riether |
| 2015/0276777 A1 | 10/2015 | Riether et al. |
| 2015/0276778 A1 | 10/2015 | Riether et al. |
| 2015/0276781 A1 | 10/2015 | Riether et al. |
| 2015/0276782 A1 | 10/2015 | Riether |
| 2015/0360876 A1 | 12/2015 | Sinz |
| 2015/0360878 A1 | 12/2015 | Denninger et al. |
| 2016/0003859 A1 | 1/2016 | Wenczel et al. |
| 2016/0025756 A1 | 1/2016 | Pollack et al. |
| 2016/0054341 A1 | 2/2016 | Edelmann |
| 2016/0054344 A1 | 2/2016 | Heise et al. |
| 2016/0069715 A1 | 3/2016 | Sinz |
| 2016/0077120 A1 | 3/2016 | Riether |
| 2016/0097786 A1 | 4/2016 | Malinowski et al. |
| 2016/0229565 A1 | 8/2016 | Margner |
| 2016/0274137 A1 | 9/2016 | Baer |
| 2016/0282378 A1 | 9/2016 | Malinowski et al. |
| 2016/0341750 A1 | 11/2016 | Sinz et al. |
| 2016/0341751 A1 | 11/2016 | Huber et al. |
| 2017/0096307 A1 | 4/2017 | Mahmudimanesh et al. |
| 2017/0097372 A1 | 4/2017 | Heise et al. |
| 2017/0101277 A1 | 4/2017 | Malinowski |
| 2017/0108522 A1 | 4/2017 | Baer |
| 2017/0131307 A1 | 5/2017 | Pedain |
| 2017/0131309 A1 | 5/2017 | Pedain |
| 2017/0131310 A1 | 5/2017 | Volz et al. |
| 2017/0160299 A1 | 6/2017 | Schneider et al. |
| 2017/0168079 A1 | 6/2017 | Sinz |
| 2017/0174448 A1 | 6/2017 | Sinz |
| 2017/0184622 A1 | 6/2017 | Sinz et al. |
| 2017/0248623 A1 | 8/2017 | Kaeppeli et al. |
| 2017/0248624 A1 | 8/2017 | Kaeppeli et al. |
| 2017/0363608 A1 | 12/2017 | Sinz |
| 2018/0067141 A1 | 3/2018 | Mahmudimanesh et al. |
| 2018/0106821 A1 | 4/2018 | Vollenweider et al. |

(56) References Cited

U.S. PATENT DOCUMENTS

| | | |
|---|---|---|
| 2018/0128848 A1 | 5/2018 | Schneider et al. |
| 2018/0156835 A1 | 6/2018 | Hassan |
| 2018/0188280 A1 | 7/2018 | Malinowski |
| 2018/0210000 A1 | 7/2018 | van Mierlo |
| 2018/0210001 A1 | 7/2018 | Reza |
| 2018/0217174 A1 | 8/2018 | Malinowski |
| 2018/0217176 A1 | 8/2018 | Sinz et al. |
| 2018/0224476 A1 | 8/2018 | Birrer et al. |
| 2018/0348244 A1 | 12/2018 | Ren |
| 2018/0348245 A1 | 12/2018 | Schneider et al. |
| 2019/0018027 A1 | 1/2019 | Hoehnel |
| 2019/0076845 A1 | 3/2019 | Huber et al. |
| 2019/0076846 A1 | 3/2019 | Durco et al. |
| 2019/0086433 A1 | 3/2019 | Hermann et al. |
| 2019/0094251 A1 | 3/2019 | Malinowski |
| 2019/0094252 A1 | 3/2019 | Waser et al. |
| 2019/0101468 A1 | 4/2019 | Haldar |

FOREIGN PATENT DOCUMENTS

| | | |
|---|---|---|
| DE | 3909786 A1 | 9/1990 |
| DE | 102012000665 A1 | 8/2012 |
| DE | 102011090044 A1 | 7/2013 |
| EP | 0601213 A1 | 10/1992 |
| EP | 0775650 A1 | 5/1997 |
| EP | 0916406 A2 | 5/1999 |
| EP | 1122194 A1 | 8/2001 |
| EP | 1524525 A1 | 4/2005 |
| EP | 2119643 A1 | 11/2009 |
| EP | 2148117 A1 | 1/2010 |
| EP | 2327646 A1 | 6/2011 |
| EP | 2447701 A2 | 5/2012 |
| EP | 2500871 A1 | 9/2012 |
| EP | 2502675 B1 | 2/2014 |
| EP | 2887071 A1 | 6/2015 |
| GB | 2165515 A | 4/1986 |
| JP | S56-147209 A | 11/1981 |
| JP | 60-223481 A | 11/1985 |
| JP | 61-081323 A | 4/1986 |
| JP | S61-069604 A | 4/1986 |
| JP | S61-094925 A | 5/1986 |
| JP | S61-174031 A | 8/1986 |
| JP | S61-217434 A | 9/1986 |
| JP | S62-100161 A | 5/1987 |
| JP | S63-31918 A | 2/1988 |
| JP | S63-48169 A | 2/1988 |
| JP | S63-82433 U | 5/1988 |
| JP | S63-290101 A | 11/1988 |
| JP | 1148966 A | 6/1989 |
| JP | H01-266860 A | 10/1989 |
| JP | H02-87903 A | 3/1990 |
| JP | 03-112393 A | 5/1991 |
| JP | 03-192013 A | 8/1991 |
| JP | H03-38704 Y2 | 8/1991 |
| JP | H04-127063 A | 4/1992 |
| JP | H05-69350 A2 | 3/1993 |
| JP | H05-142232 A | 6/1993 |
| JP | H05-180847 A | 7/1993 |
| JP | 06-26808 A | 2/1994 |
| JP | H06-84180 A | 3/1994 |
| JP | H06-148198 A | 5/1994 |
| JP | 06-156730 A | 6/1994 |
| JP | 06-211306 A | 8/1994 |
| JP | 07-228345 A | 8/1995 |
| JP | 07-236838 A | 9/1995 |
| JP | H07-301637 A | 11/1995 |
| JP | H09-17848 A | 1/1997 |
| JP | H11-083865 A | 3/1999 |
| JP | H11-264828 A | 9/1999 |
| JP | H11-304812 A | 11/1999 |
| JP | H11-326336 A | 11/1999 |
| JP | 2000-105243 A | 4/2000 |
| JP | 2000-105246 A | 4/2000 |
| JP | 2001-124786 A | 5/2001 |
| JP | 2001-240245 A | 9/2001 |
| JP | 2005-001055 A | 1/2005 |
| JP | 2005-249740 A | 9/2005 |
| JP | 2006-106008 A | 4/2006 |
| JP | 2007-309675 A | 11/2007 |
| JP | 2007-314262 A2 | 12/2007 |
| JP | 2007-322289 A | 12/2007 |
| JP | 2009-036643 A | 2/2009 |
| JP | 2009-062188 A | 3/2009 |
| JP | 2009-145188 A | 7/2009 |
| JP | 2009-300402 A | 12/2009 |
| JP | 2010-243310 A | 10/2010 |
| JP | 2010-271204 A | 12/2010 |
| JP | 2013-172009 A2 | 2/2013 |
| JP | 2013-190400 A | 9/2013 |
| SU | 685591 A1 | 9/1979 |
| WO | 1996036437 A1 | 11/1996 |
| WO | 2003042048 A3 | 5/2003 |
| WO | 2007024540 A1 | 3/2007 |
| WO | 2008133708 A1 | 11/2008 |
| WO | 2009002358 A1 | 12/2008 |
| WO | 2010042722 A1 | 4/2010 |
| WO | 2012170636 A1 | 7/2010 |
| WO | 2010087303 A1 | 8/2010 |
| WO | 2010129715 A1 | 11/2010 |
| WO | 2012158520 A1 | 11/2012 |
| WO | 2012158541 A1 | 11/2012 |
| WO | 2013152089 A1 | 10/2013 |
| WO | 2013169778 A1 | 11/2013 |
| WO | 2013177163 A1 | 11/2013 |
| WO | 2014059134 A1 | 4/2014 |
| WO | 2014071214 A1 | 5/2014 |

| | | | | | |
|---|---|---|---|---|---|
| t=0 | 5_1=OFF | 5_2=ON | 5_3=OFF | 5_4=OFF | 5_5=OFF |
| t=1 | 5_1=OFF | 5_2=OFF | 5_3=ON | 5_4=OFF | 5_5=OFF |
| t=2 | 5_1=OFF | 5_2=OFF | 5_3=OFF | 5_4=ON | 5_5=OFF |

LABORATORY SAMPLE DISTRIBUTION SYSTEM AND CORRESPONDING METHOD OF OPERATION

CROSS-REFERENCE TO RELATED APPLICATIONS

This application is a continuation of patent application Ser. No. 14/262,945, filed on Apr. 28, 2014, now allowed, which is a continuation of PCT/EP2012/071762, filed Nov. 2, 2012, which is based on and claims priority to EP 11187977.1, filed Nov. 4, 2011, which are hereby incorporated by reference.

BACKGROUND

The present disclosure generally relates to a laboratory sample distribution system and a corresponding method of operation.

Laboratory sample distribution systems are used to distribute samples or specimens, for example, blood samples or specimens, between various different laboratory stations or specimen-processing instruments, such as pre-analytical stations, analytical stations and post-analytical stations.

In one prior art system, a drive mechanism which operates to advance specimen-container racks on a surface by producing an X/Y movable magnetic field below the surface. The movable magnetic field is produced by permanent magnets carried by an X/Y movable magnetic truck assembly. The magnetic field produced by each magnet magnetically couples with magnetically-attractive members carried in a base portion of each specimen-transport rack. The magnetic bond between the magnets and magnetically-attractive members is sufficiently strong that, as the magnetic truck assembly moves in the X/Y plane, a magnetically-coupled rack follows. Due to mechanical constraints caused by the X/Y movable magnetic truck assembly independent simultaneous movements of multiple specimen-transport racks are difficult to implement. Further, specimen-containers can only be moved together in specimen-transport rack quantities.

Therefore, there is a need to provide a laboratory sample distribution system and a corresponding method of operation that is highly flexible and offers a high transport performance.

SUMMARY

According to the present disclosure, a laboratory sample distribution system is presented. The system comprises a plurality of container carriers. Each container carrier can comprise at least one magnetically active device and can carry a sample container. The system can further comprise a transport plane to carry the container carriers and a plurality of electro-magnetic actuators stationary arranged below the transport plane. The electro-magnetic actuators can move a container carrier on top of the transport plane by applying a magnetic force to the container carrier.

Accordingly, it is a feature of the embodiments of the present disclosure to provide a laboratory sample distribution system and a corresponding method of operation that is highly flexible and offers a high transport performance. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
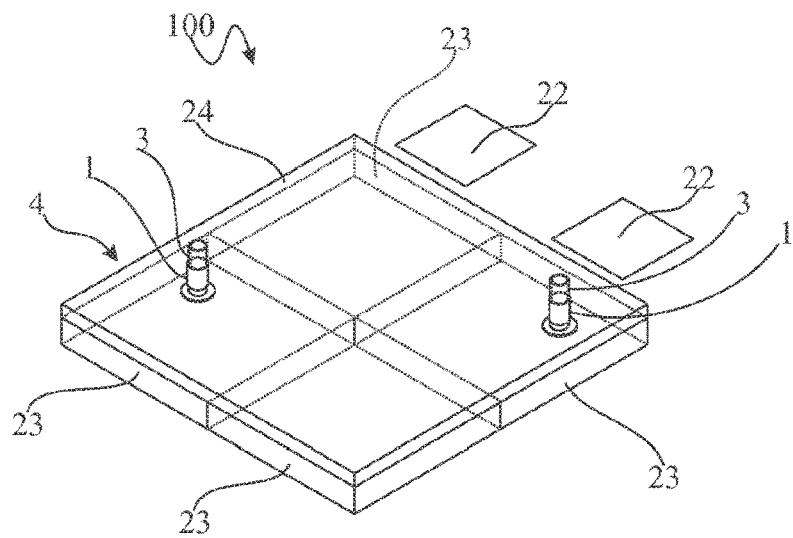
FIG. 1 illustrates a laboratory sample distribution system having a transport plane formed by multiple sub planes according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A laboratory sample or specimen distribution system according to a first embodiment can comprise a plurality of container carriers such as, for example about 50 to about 500 container carriers. The container carriers cannot be self-powered. The container carriers can comprise at least one magnetically active, i.e. magnetically attractive, device and can carry a single sample container. Further, the system can comprise a two dimensional transport plane or supporting surface, which may be completely planar and can carry at least part of the container carriers. A number of electro-magnetic actuators such as, for example about 50 to about 5000 electro-magnetic actuators, can be arranged stationary or fixed below the transport plane. The electro-magnetic actuators can move a container carrier on top of the transport plane in at least two different directions by applying or causing a magnetic force to the container carrier, i.e. to the magnetically active device of the container carrier.

The transport plane can support the container carriers in a way to allow movement along directions as guided by magnetic forces. Accordingly, the transport plane can be continuous in at least those directions of movements to allow a smooth travel of the container carriers. In order to allow a flexible transfer of carriers along many lateral directions, a flat transport plane can be an advantage. On a microscopic level, it can be advantageous to employ a surface with many small protrusions in order to reduce friction between the transport plane and the bottom surface of the container carrier.

The transport plane can further transmit the magnetic field of the electro-magnetic actuators. Accordingly, the transport plane can be made from magnetically transmissive materials such as, for example, glass or plastics. Further, the thickness of the transport plane can be a compromise between mechanical stability and magnetic shielding. A transport plane having a thickness of about 2 to about 10 mm can be well suited.

The magnetically active device can be a device to cause magnetic forces in interaction with a corresponding magnetic field. The magnetically active device may comprise at least one permanent magnet. By the multiple electro-magnetic actuators interacting individually with corresponding container carriers, it can be possible to independently and simultaneously move multiple individual sample containers along a given grid over the transport plane offering high transport flexibility, which can mean that single containers can be transported independently from each other to desired locations on the transport plane.

The transport plane may be formed of multiple adjacent sub-planes. The system may comprise a cover profile covering the transport plane, i.e. covering the sub-planes forming the transport plane. The cover profile can simplify the cleaning of the transport plane and can avoid disturbing gaps between adjacent sub-planes. Further, the cover profile can mitigate height differences between adjacent sub-planes. The cover profile may be fluidtight. The cover profile may be just overlying the transport plane or may be glued to the top surface of the sub-planes to stabilize the arrangement and to prevent spacing which can reduce magnetic forces.

The cover profile may be a glass plate, a non-magnetic metal plate such as, for example, an aluminum plate, or a foil of plastic material such as, for example, a foil of polyethylene or PTFE (poly-tetra-fluoro-ethylene). A glass plate can be chemically resistant, easily washable and stiff, so that height differences between sub-planes may be mitigated. For flexible cover profiles, a suitable thickness of the cover profile can be a compromise between mechanical stability, height mitigation and magnetic shielding. In the case of plastic materials, a cover profile having a thickness of about 1 to about 10 mm can be well suited.

The surface of the container carriers and the surface of the transport plane, i.e. the surface of the cover profile, may be arranged to reduce friction between the surfaces, for example, by coating the container carriers and/or the transport plane or cover profile and/or by roughening the contact surfaces of the container carriers and/or of the cover profile.

The electro-magnetic actuators may be arranged in rows and columns forming a grid having a given, for example, constant, grid dimension. The grid dimension can specify a distance between adjacent or consecutive electro-magnetic actuators in a given row or column.

The container carriers may have a stand. The stand may have a circular cross section having a diameter that is equal to or less than the grid dimension. This dimensioning can make it possible that two carriers moving on direct adjacent rows or columns formed by electro-magnetic actuators can pass by each other without collision.

The electro-magnetic actuators may be arranged in rows and columns forming a grid or matrix. Adjacent rows may have different grid dimensions selected either from a first grid dimension or a second grid dimension and adjacent columns may have different grid dimensions selected either from the first grid dimension or the second grid dimension, wherein the second grid dimension is larger, for example, twice as large, as the first grid dimension.

The container carriers each can have a stand. The stand can have a circular cross section having a diameter that can be equal to or less than the larger grid dimension.

The circular cross section of the stand can reduce the likelihood of a stand collision of container carriers moving adjacent in different directions. Compared, for example, with quadratic stands, this can reduce the required safety distance between adjacent positions and the requirements on positioning accuracy. Further, the circular stand can improve the self-supporting of the container carrier, for example, can prevent that the containers carrier tilts under normal operating conditions.

The dimensioning of the size or diameter of the stand smaller than or equal to the larger grid dimension (i.e. the distance between the electro-magnetic actuators forming the larger grid), wherein the larger grid dimension can be twice as large as the first grid dimension, can make it possible that two carriers moving on adjacent tracks formed by electro-magnetic actuators arranged according to the smaller grid dimension can pass by each other without collision. On the other hand, the footprint can be large enough to provide a smooth transport without much tilting.

The electro-magnetic actuators may be arranged in rows and columns forming a grid or matrix of active transport fields. The rows and columns can have either a first grid dimension g1 or a second grid dimension g2, wherein $g2=2*g1$. Adjacent rows and adjacent columns can have different grid dimensions. The grid dimension can specify a distance between adjacent or consecutive electro-magnetic actuators in a given row or column. In other words, the electro-magnetic actuators can be arranged in the form of a grid or matrix, wherein the grid or matrix can have blank positions representing omitted electro-magnetic actuators. This arrangement can consider that diagonal movements of the container carriers may not be necessary to reach a specific destination on the transport plane, since the specific destination can be reached based on movements along the rows and columns. This arrangement of the electro-magnetic actuators can reduce the number of required electro-magnetic actuators significantly (by, for example, 33%) compared to a solution having a constant grid dimension. Nevertheless, if a diagonal movement is required, it can be self-evident that the rows and columns may be provided having a constant grid dimension, for example, forming a transport plane being divided in active transport fields with equal dimensions.

If the transport plane is divided into multiple sub-planes, each sub-plane may have a first outer face, a second outer face, a third outer face and a fourth outer face at which further planes can be arranged in a tiling manner to form a transport plane. This approach can offer the ability to provide transport planes of desired shape. This can be a big advantage to serve the needs an individual laboratory might have due to the laboratory stations present or due to spatial restraints.

The approach to build the transport plane from sub-planes can be combined with the concept of rows having different grid dimensions to reduce the number of needed electro-magnetic actuators. Sub-planes can be employed where along the first and the second outer face the electro-magnetic actuators can be arranged in a first grid dimension g1 and along the third and the fourth outer face the electro-magnetic actuators can be arranged in a second grid dimension g2, wherein g2=2*g1. Multiple sub-planes can be arranged adjacent in a tiling manner to form the transport plane, wherein adjacent outer faces of different sub-planes have different grid dimensions.

The container carriers each may have a stand. The stand can have a circular cross section covering approximately five electro-magnetic actuators if positioned in the center of a cross formed by five electro-magnetic actuators. The electro-magnetic actuator in the center of the cross may be fully covered wherein the four outer electro-magnetic actuators may be covered by half if the stand is positioned in the center of the cross formed by the five electro-magnetic actuators. The stand may have a diameter in the range of about 3.5 cm to about 4.5 cm.

The ratio between the size or diameter of the stand relative to the distance between the electro-magnetic actuators can make it possible that two carriers moving on adjacent tracks can pass by each other without collision. On the other hand, the footprint can be large enough to provide a smooth transport without much tilting.

Each electro-magnetic actuator may comprise a ferromagnetic core. The ferromagnetic core can cause a holding force acting on the at least one magnetically active device of a container carrier placed on top of the electro-magnetic actuator if the electro-magnetic actuator is not driven by an actuating current.

The at least one permanent magnet may be ball-shaped, wherein a north pole or a south pole of the ball-shaped permanent magnet can be directed to the transport plane. In other words, an axis extending through the opposite poles of the ball-shaped permanent magnet can be perpendicular to the transport plane. A diameter of the ball-shaped permanent magnet may be approximately 12 mm. The ball-shaped permanent magnet can cause an optimized magnetic field in interaction with the electro-magnetic actuators, e.g. compared with a bar magnet, resulting in higher magnetic force components in a lateral movement direction.

The permanent magnet in conjunction with a ferromagnetic core of a currently adjacent non-activated electro-magnetic actuator can cause an unwanted magnetic retention force. The retention force can hinder the desired movement of the container carrier away from the currently adjacent non activated electro-magnetic actuator towards an activated electro-magnetic actuator. Increasing the distance between the permanent magnet and the transport plane, i.e. also increasing the distance between the permanent magnet and the electro-magnetic actuators, can reduce this magnetic retention force. Unfavorably, an increasing distance can also lower a desired magnetic transport force in a lateral movement direction. Therefore, a distance between a center of the at least one permanent magnet and a bottom surface of the container carrier, the bottom surface in contact with the transport plane, may be selected within a range of about 5 mm to about 50 mm. The given distance range can provide an optimized compromise between a desired magnetic transport force in movement direction and an unwanted magnetic retention force.

The container carriers may comprise a first permanent magnet arranged in the center of a stand of the container carrier and a second permanent magnet having a ring shape arranged in the stand surrounding the first permanent magnet. This arrangement can provide high flexibility in causing push and pull magnetic forces, especially if more than one electro-magnetic actuator is activated at a given time. The first and second permanent magnets may have a reverse polarity, i.e. a south pole of the first permanent magnet and a north pole of the second permanent may point to the transport plane, or vice versa. The ring shaped second permanent magnet may constitute a circular area having a diameter that can be smaller than a distance between axes of electro-magnetic actuators of the transport plane.

The container carriers may comprise a RFID tag storing a unique ID. This can enable matching a sample container ID, e.g. a barcode, with the corresponding container carrier. The unique carrier ID can be read by an optional RFID reader being part of the system and being placed at one or more specific locations within the system.

The RFID tag may comprise a ring shaped antenna arranged in a stand of the container carrier. This antenna arrangement can make it possible to read the RFID tag by a RFID reader antenna below the transport plane. Thus, the transport plane itself and/or areas above the transport plane may be designed free of any disturbing RFID reader antennas.

The electro-magnetic actuators may comprise a ferromagnetic core guiding and amplifying a magnetic field. The electro-magnetic actuators may have a center finger and four outer fingers, each of the fingers extending perpendicular to the transport plane. Only the center finger may be surrounded by a coil driven by an actuating current. This arrangement can reduce the number of coils needed for activating the electro-magnetic actuators, wherein the center finger and the outer fingers can interact advantageously by providing push and pull forces, respectively, especially if the container carrier comprises a first permanent magnet arranged in the center of the stand and a second permanent magnet having a ring shape arranged in the stand surrounding the first permanent magnet.

The system may further comprise a container carrier sensing device to sense the presence and position of container carriers located on the transport plane. The container carrier sensing device can provide for an optimized tracking of container carriers placed on top of the transport plane.

The container carrier sensing device may be embodied based on infra-red (IR) based reflection light barriers. These light barriers may be arranged in recesses in the transport plane or may be arranged below a transport plane which can be at least partially transparent for the employed light. In the latter case, a closed transport plane can be provided which inter alia can be easier to clean.

The system may comprise a magnetizable coupling element to provide a magnetic coupling between adjacent electro-magnetic actuators. Due to the coupling element, the activated electro-magnetic actuator can automatically cause a magnetic field in the adjacent actuators having an inverse polarization. This can automatically provide respective pull and push forces even if only a single electro-magnetic actuator is activated, e.g. by a corresponding activating current.

The system may comprise a security cover to cover the transport plane and the container carriers placed on the transport plane. The security cover can cover the transport plane and the container carriers placed on the transport plane such that the container carriers can move unhindered over the transport plane. The security cover may e.g. be made of transparent plastic. The security cover can prevent contamination and unintentional access to the transport plane. The security cover may have a footprint which can be approximately equal to the footprint of the transport plane.

The security cover may have an open state and a closed state, wherein in the open state, the transport plane or dedicated areas of the transport plane may be accessible by a user and in the closed state, the transport plane may not be accessible by a user, thereby preventing damage and/or manual access causing unwanted positions of container carriers placed on the transport plane. The security cover may have flaps or sections operable such that specific sections/areas on the transport plane can be accessible. The security cover can further prevent pollution of the transport plane.

A method for the versatile transport of sample containers can be achieved with a laboratory sample distribution system comprising a number of container carriers as described above. The container carriers can comprise at least one magnetically active device and can carry a sample container. The laboratory sample distribution system can further comprise a transport plane to carry the container carriers and a number of electro-magnetic actuators being stationary arranged below the transport plane. The electro-magnetic actuators can move a container carrier on top of the transport plane by applying a magnetic force to the container carrier. The method can comprise activating at least one of the electro-magnetic actuators to apply a magnetic force to a container carrier within an operating distance of the at least one activated electro-magnetic actuator. Activating an electro-magnetic actuator can mean that a magnetic field can be generated by the electro-magnetic actuator. Activating may be done by generating a driving current applied to a coil surrounding a ferromagnetic core.

The speed of a container carrier moving across the transport plane may be set by setting a period between a successive activation of adjacent electro-magnetic actuators. If this duration is set shorter, the speed can increase and vice versa. By changing the duration dynamically, a container carrier may be accelerated or slowed down.

The electro-magnetic actuators may be activated in response to a sensed position of the container carrier to be applied with the magnetic force. The electro-magnetic actuators may be activated such that a polarity of the generated magnetic field can depend on a position of the container carrier relative to the electro-magnetic actuator. This can cause position-depended pull and push forces. In a first position range when the container carrier is moving towards the activated electro-magnetic actuator, the pull force may attract the container carrier towards the activated electro-magnetic actuator. In a second position range when the container carrier has traversed the electro-magnetic actuator, the push force may push the container carrier away from the activated electro-magnetic actuator now generating a magnetic field having an opposite polarity. Additionally, the magnetic field strength may be changed in response to the sensed position to provide a steady movement of the container carrier. The electro-magnetic actuators may be adapted to generate magnetic fields having only a single polarity to simplify the system. In this case, the activated electro-magnetic actuator may generate the pull force in the first position range when the container carrier is moving towards the activated electro-magnetic actuator. In the second position range when the container carrier has traversed the electro-magnetic actuator the electro-magnetic actuator may be deactivated.

For moving a first container carrier along a first transport path, a first group of electro-magnetic actuators may be activated along the first transport path. For independently and at least partially simultaneously moving a second container carrier along a second transport path, a second group of multiple electro-magnetic actuators may be activated along the second transport path. "Simultaneously" can indicate that during a certain time interval both the first and the second container carrier can move. The electro-magnetic actuators of the first or the second group may be activated one after the other along the respective transport path. Alternatively, two or more adjacent electro-magnetic actuators along the respective transport path may be activated at least partially overlapping in time.

A movement of a container carrier placed on a field on top of a first electro-magnetic actuator to an adjacent field on top of a second electro-magnetic actuator may comprise activating the first and the second electro-magnetic actuator and a third electro-magnetic actuator adjacent to the first electro-magnetic actuator and opposite to the second electro-magnetic actuator and part of the same row or column as the first and the second electro-magnetic actuators in a predetermined order.

If the container carriers comprise a first permanent magnet arranged in the center of a stand of the container carrier and a second permanent magnet having a ring shape arranged in the stand surrounding the first permanent magnet the method may further comprise activating the second electro-magnetic actuator such that a resulting pull-force regarding the second permanent magnet having a ring shape can be generated and activating the third electro-magnetic actuator such that a resulting push-force regarding the second permanent magnet can be generated; after a predetermined time interval or at a predetermined position of the container carrier: activating the first electro-magnetic actuator such that a resulting pull-force regarding the second permanent magnet can be generated and that a resulting push-force regarding the first permanent magnet can be generated; and after a second predetermined time interval or at a second predetermined position of the container carrier: activating the second electro-magnetic actuator such that a resulting pull-force regarding the second permanent magnet can be generated. A movement between adjacent electro-magnetic actuators can be done in a sequence of three activation patterns regarding three adjacent electro-magnetic actuators. This can lead to a continuous uniform movement with a high positioning accuracy. The first and second time interval or the first and the second position may be determined based on a sensed position of the container carrier provided by the container carrier sensing device.

Referring initially to FIG. 1, FIG. 1 shows a laboratory sample distribution system 100. The laboratory sample distribution system 100 can be used to distribute samples or specimens, e.g. blood samples, contained within sample containers or sample tubes 3 between different laboratory stations or specimen-processing instruments 22, such as pre-analytical stations, analytical stations and post-analytical stations typically used in laboratory systems.

The laboratory sample distribution system 100 can comprise a number of container carriers or Single-Tube-Carriers 1 each can carry a corresponding sample container 3 over a transport plane 4. Multiple electro-magnetic actuators 5 (see FIGS. 2 and 3) can be stationary arranged below the transport plane 4. Each of the electro-magnetic actuators 5 can move a container carrier 1 in operating distance of a corresponding electro-magnetic actuator 5 by applying a magnetic force to the container carrier 1.

The depicted transport plane 4 can be divided into four quadratic sub-planes 23, the sub-planes 23 can be adjacent to one another. The transport plane can be covered by an optional cover profile 24, the cover profile 24 can be fluidtight and can cover gaps and mitigate height differences between adjacent sub-planes 23. The material of the cover profile 24 can provide a low friction coefficient. The cover profile 24 may e.g. be a glass plate or a foil of polyethylene or PTFE (poly-tetra-fluoro-ethylene).

Figure 2:
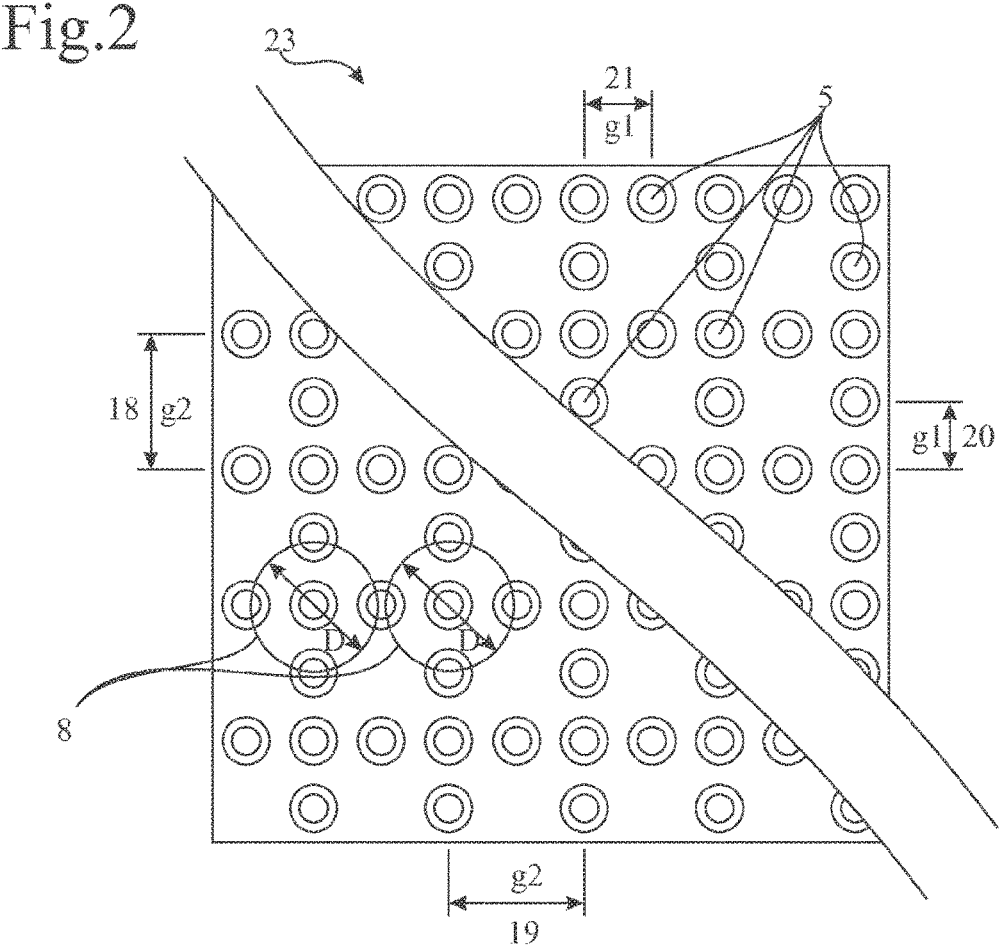
FIG. 2 illustrates a top view of an exemplary sub plane shown in FIG. 1 according to an embodiment of the present disclosure.

FIG. 2 shows a schematic top view on an exemplary sub-plane 23 of FIG. 1. The sub-plane can have a first outer face 20, a second outer face 21, a third outer face 18 and a fourth outer face 19. Along the first and the second outer face 20 and 21, the electro-magnetic actuators 5 can be arranged in a first grid dimension g1. Along the third and the fourth outer face 18 and 19, the electro-magnetic actuators 5 can be arranged in a second grid dimension g2, wherein g2=2*g1. The grid dimension g1 may e.g. be about 20 mm.

The electro-magnetic actuators 5 can be arranged in rows and columns, for example, 16 rows and 16 columns, the rows and columns having either a first grid dimension g1 or a second grid dimension g2, wherein g2=2*g1, and adjacent rows having a different grid dimension and adjacent columns having a different grid dimension. If a position or field on the transport plane has to be accessible as a target destination, a corresponding electro-magnetic actuator can be provided below that target destination. If a specific field or area has not to be accessible, an electro-magnetic actuator may be omitted at that position.

FIG. 2 depicts two exemplary container carriers each having a stand 8 with a circular cross section having a diameter D that is approximately 1% to 20% smaller than the larger grid dimension g2. Due to this, two carriers moving on adjacent tracks can pass by each other without collision. On the other hand, the footprint can be large enough to provide a smooth transport without much tilting.

Figure 3:
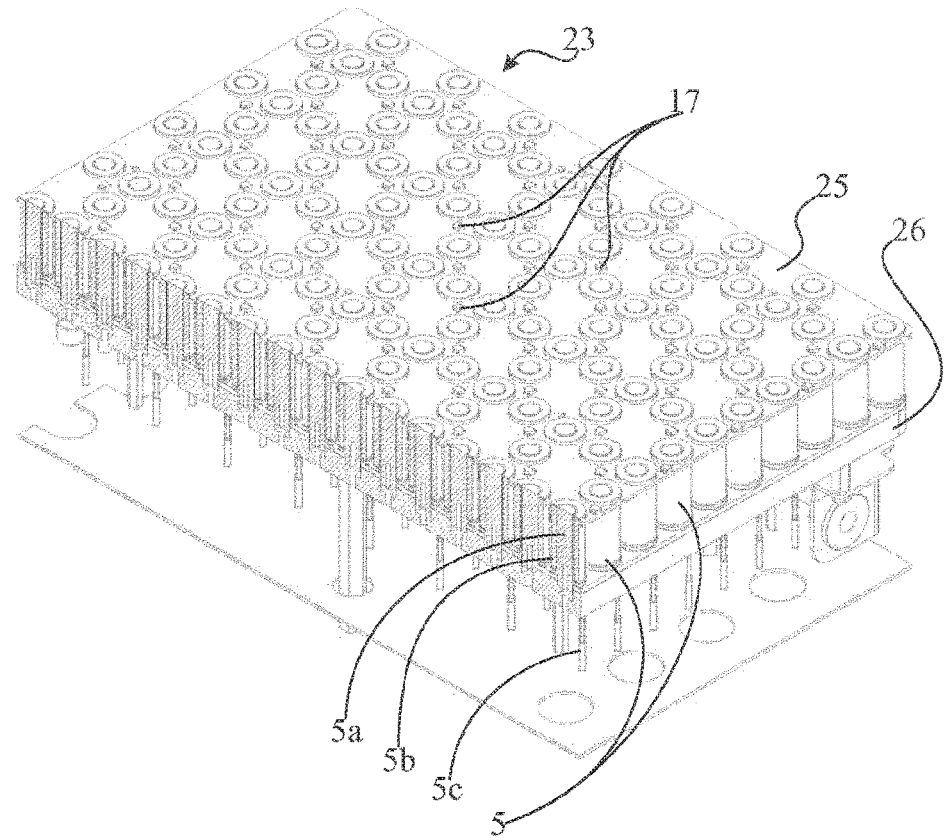
FIG. 3 illustrates a detailed perspective side view of the sub plane shown in FIG. 2 according to an embodiment of the present disclosure.

FIG. 3 shows detailed perspective side view of the sub-plane 23 shown in FIG. 2. As illustrated, each electro-magnetic actuator 5 can be fixed on a carrier plate 26 and can comprise a ferro-magnetic cylindrical core 5a extending basically perpendicular to the transport plane 4. A coil 5b can surround the ferro-magnetic cylindrical core 5a. The coil 5b can be applied with an actuating current provided by a driver unit (not shown) over electrical contacts 5c. If driven by an actuating current, each electro-magnetic actuator 5 can generate a magnetic field. When this field interacts with a permanent magnet 2 (see FIG. 4) in the container carrier 1, it can provide a driving force moving the container carrier 1 along the transport plane 4. The ferro-magnetic cylindrical core 5a can bundle and amplify the magnetic field generated by the coil 5b.

In the most simple form, each container carrier 1 may be exposed to a driving force generated by a single activated electro-magnetic actuator 5 proximate to the corresponding container carrier 1 thereby pulling the container carrier 1 towards the activated electro-magnetic actuator 5. Further, it can be possible to superpose push and pull driving forces of multiple electro-magnetic actuators 5 proximate to the corresponding container carrier 1.

Further, it can be possible to activate multiple electro-magnetic actuators 5 at the same time to move multiple different container carriers 1 independent of each other along predetermined paths over the transport plane 4.

In order to sense the presence and position of container carriers 1 located on the transport plane 4, a container carrier sensing device can be provided. One embodiment can comprise a printed circuit board 25 having multiple IR based reflection light barriers 17 arranged in a grid on top as shown in FIG. 3.

The IR based reflection light barriers 17 can detect container carriers 1 placed on top of a corresponding light barrier 17 since the container carriers 1 can be arranged to reflect IR radiation emitted by the light barriers 17. If no container carrier is present, no reflected IR light can get into the IR sensor of a corresponding light barrier 17.

Figure 4:
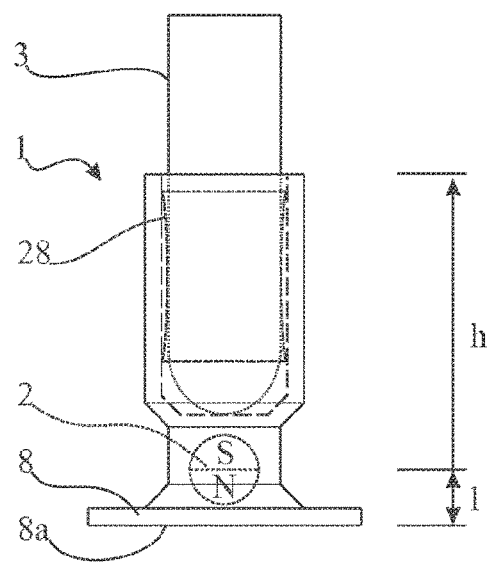
FIG. 4 illustrates a container carrier according to a first embodiment of the present disclosure.

FIG. 4 shows a container carrier 1 according to a first embodiment. The container carrier 1 can comprise a ball-shaped permanent magnet 2. A distance 1 between a center of the at least one permanent magnet 2 and a bottom surface 8a of the container carrier, the bottom surface 8a can be in contact with the transport plane 4, can lie within a range of about 5 mm to about 50 mm and may be approximately 12 mm. A height h of the container carrier 1 may be approximately 42 mm.

The permanent magnet 2 may be made from hard ferro-magnetic materials. These can include e.g. iron ore (magnetite or lodestone), cobalt and nickel, as well as the rare earth metals. A north pole N of the permanent magnet 2 can be directed towards the transport plane.

A stand 8 of the container carrier can have a circular cross section having a diameter of approximately 3.5 cm to 4.5 cm covering approximately five electro-magnetic actuators 5 if positioned in the center of a cross formed by the five electro-magnetic actuators 5. The electro-magnetic actuator in the center of the cross can be fully covered, wherein the four outer electro-magnetic actuators can be nearly covered by half. Due to this, two carriers moving on adjacent tracks can pass by each other without collision. On the other hand, the footprint can be large enough to provide a smooth transport without much tilting.

The container carriers may comprise a sample container fixer which may e.g. be incorporated in form of flexible flat spring 28. The flexible flat spring 28 can be at the side wall of the cylindrical opening of the container carrier 3. The flexible flat spring 28 can safely fix the sample container 3 within the container carrier 1, even if the sample container 3 has a smaller diameter than the corresponding opening.

If different sample container types are used, e.g. having different form factors, it can be even possible to provide specific container carriers with different inner diameters corresponding to respective sample container types.

Figure 5:
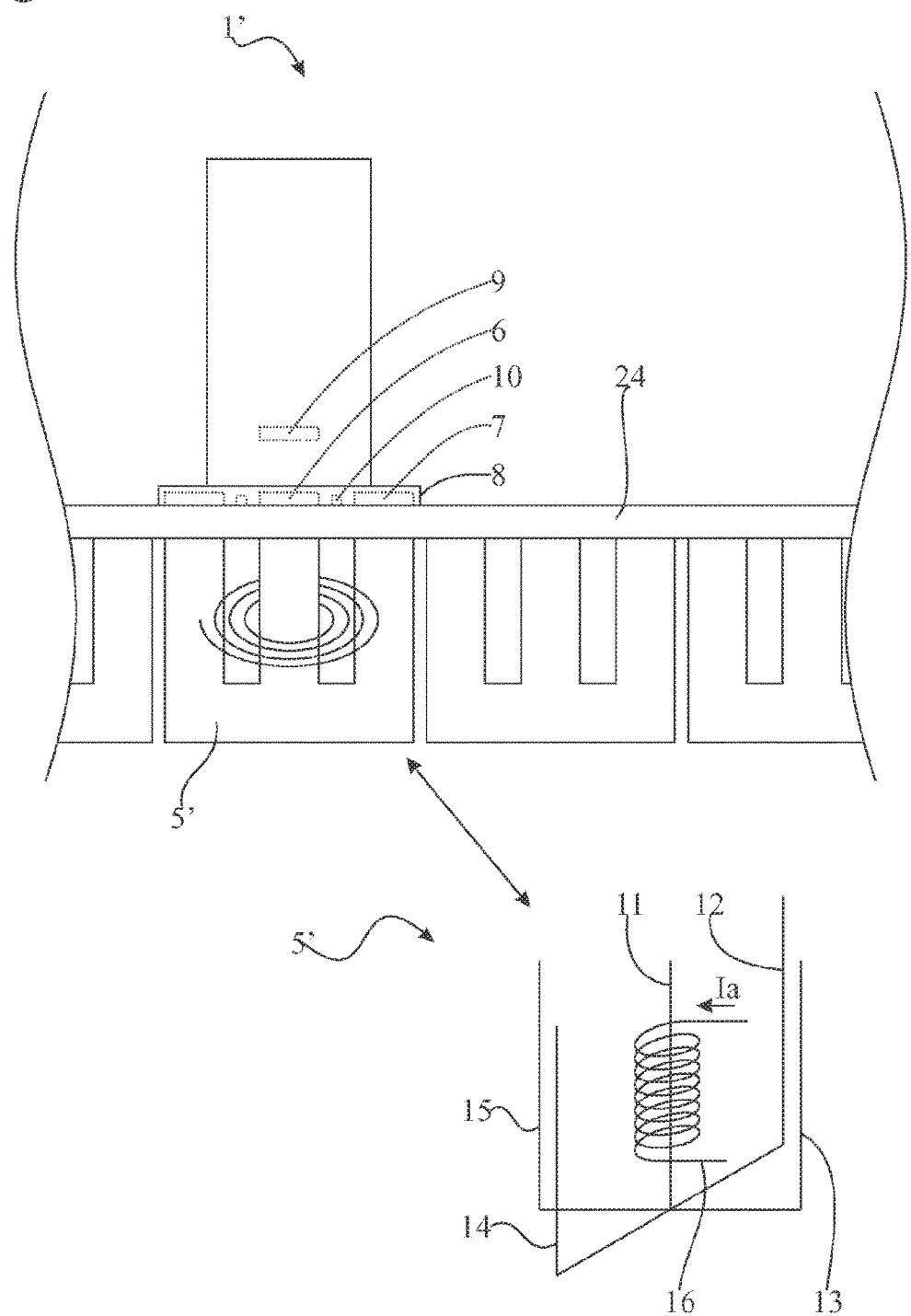
FIG. 5 illustrates a container carrier and a corresponding electro-magnetic actuator according to a second embodiment of the present disclosure.

FIG. 5 shows a container carrier 1' according to a second embodiment having a different magnet arrangement and a corresponding electro-magnetic actuator 5'. The container carrier 1' can comprise a first permanent magnet 6 arranged in the center of a stand 8 of the container carrier 1' and a second permanent magnet 7 having a ring shape arranged in the stand 8 surrounding the first permanent magnet 6. The permanent magnets 6 and 7 can have a reverse polarity. A north pole of the center permanent magnet 6 and a south pole of the ring shaped permanent magnet 7 can be directed towards the transport plane 4.

Further, the container carrier 1' can comprise a RFID tag 9 storing a unique ID corresponding to a specific container carrier. The RFID tag 9 can comprise a ring shaped antenna 10 which can be arranged in the stand 8 of the container carrier 1' between the first and the second permanent magnet 6 and 7.

The corresponding electro-magnetic actuator 5' can comprises a ferromagnetic core having a center finger 11 and four outer fingers 12, 13, 14, and 15, each of the fingers extending perpendicular to the transport plane 4, wherein only the center finger 11 can be surrounded by a coil 16 being driven by an actuating current Ia. This arrangement can reduce the number of coils needed for activating the electro-magnetic actuator 5' compared with the embodiment shown in FIG. 3, wherein the center finger 11 and the outer fingers 12 to 15 can interact advantageously by providing push and pull forces, respectively, especially if the container carrier 1' is arranged as shown.

Figure 6:
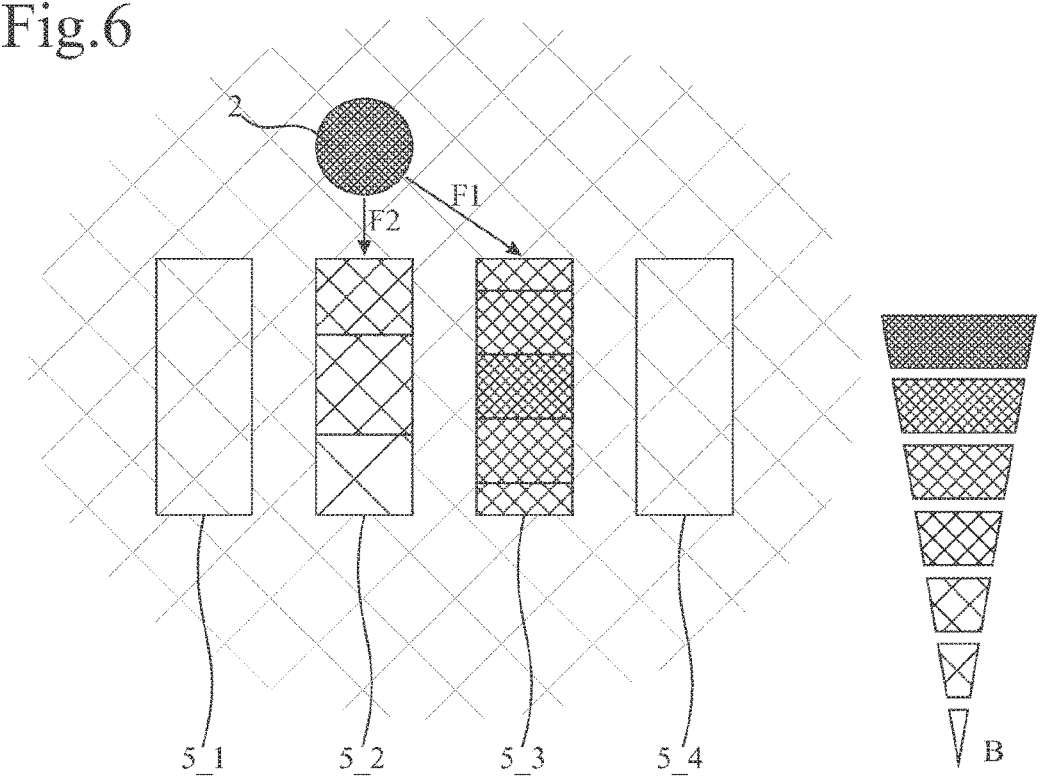
FIG. 6 illustrates a simulated magnetic flux density for a container carrier positioned on top of an electro-magnetic actuator not activated and an adjacent electro-magnetic actuator activated according to an embodiment of the present disclosure.

FIG. 6 shows a simulated magnetic flux density B for the case that a container carrier as depicted in FIG. 4 is positioned on top of an electro-magnetic actuator 5_2 not being activated and an adjacent electro-magnetic actuator 5_3 being activated. Different flux densities B can be represented by corresponding hachures.

As shown, the ball shaped permanent magnet 2 in conjunction with a ferromagnetic core of the non-activated electro-magnetic actuator 5_2 can cause an unwanted magnetic retention force F2 pulling the permanent magnet 2 towards the ferromagnetic core of the non-activated electro-magnetic actuator 5_2, thereby causing an unwanted force-component in opposite direction of the desired movement and additionally increasing friction between the corresponding surfaces of the transport plane and the stand. The activated electro-magnetic actuator 5_3 can generate a force F1.

In order to reduce these unwanted effects, it can be possible to generate an opposing magnetic field by reversely activating the electro-magnetic actuator 5_2 pushing the container carrier, thereby reducing friction. Alternatively or additionally, it can be possible to choose an optimized distance between the permanent magnet 2 and the transport plane, see also the description regarding FIG. 4. Nevertheless, the magnetic forces in a desired movement direction using a ball-shaped permanent magnet 2 can be higher compared to a bar magnet, since the resulting distances between the magnetically active spherical surface of the permanent magnet 2 and the active electro-magnetic actuator 5_3 can be smaller.

Figure 7:
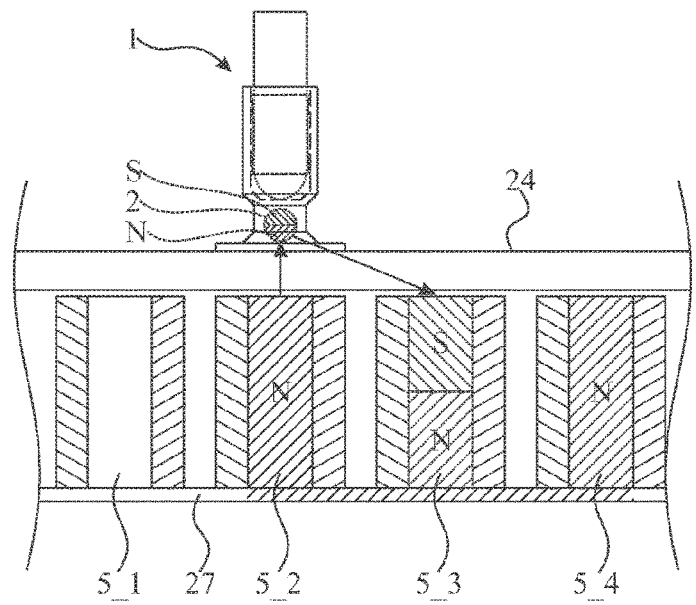
FIG. 7 illustrates a side view of an embodiment of a sub plane comprising a magnetisable coupling element providing a magnetic coupling between adjacent electro-magnetic actuators according to an embodiment of the present disclosure.

FIG. 7 shows a side view of an embodiment of a sub-plane comprising a magnetizable coupling element 27 providing a magnetic coupling between adjacent electro-magnetic actuators 5. As shown, only the electro-magnetic actuator 5_3 can be activated by driving the corresponding coil with a driving current and can cause a magnetic flow guided by the coupling element 27 and extending in the ferromagnetic cores of the non-activated electro-magnetic actuators 5_2 and 5_3. As a result, a magnetic push force can be generated by the electro-magnetic actuator 5_2 in interaction with the permanent magnet 2 reducing friction and superimposing in the desired direction with a pull force generated by the activated electro-magnetic actuators 5_3.

Figure 8:
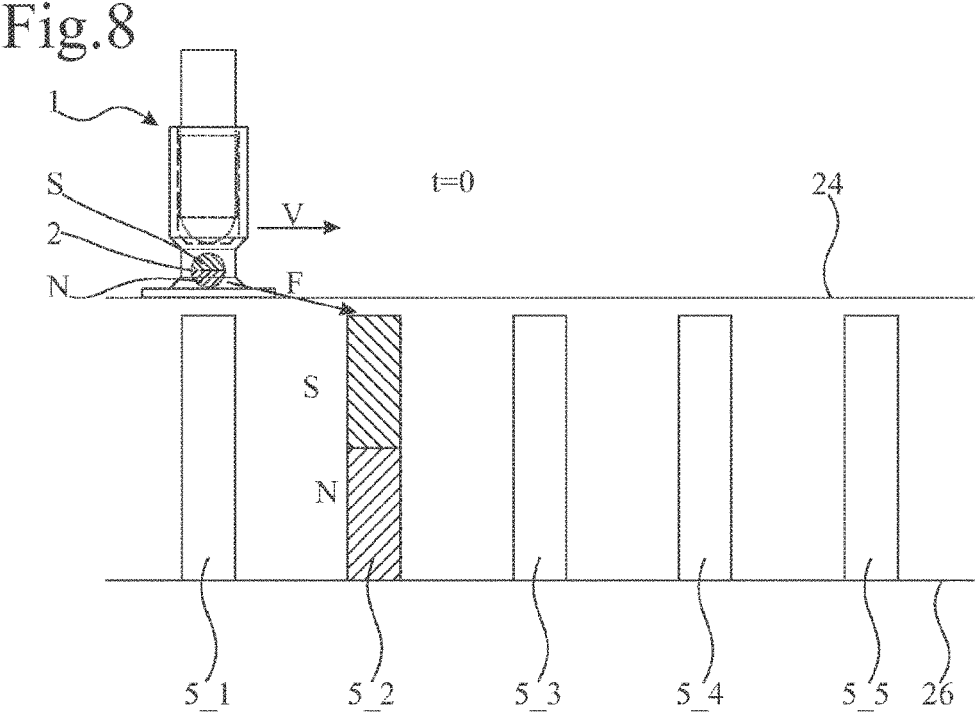
FIG. 8 illustrates movement of a container carrier and an activation order of corresponding electro-magnetic actuators according to a first embodiment of the present disclosure.

FIG. 8 shows a movement of a container carrier 1 and an activation order of corresponding electro-magnetic actuators 5_1 to 5_5 according to a first embodiment. As shown, at time t=0 only the electro-magnetic actuator 5_2 can be activated such that it can generate a pull force moving the container carrier 1 in the shown direction.

At time t=1, the container carrier 1 has moved such that it can reside on top of the electro-magnetic actuator 5_2, what e.g. can be sensed by the container carrier sensing device. In order to continue the movement electro-magnetic actuator 5_2 can be deactivated and electro-magnetic actuator 5_3 can be activated, thereby pulling the container carrier 1 forward.

At time t=2, the container carrier 1 has moved such that it can reside on top of the electro-magnetic actuator 5_3. In order to continue the movement electro-magnetic actuator 5_3 can be deactivated and electro-magnetic actuator 5_4 can be activated, thereby pulling the container carrier 1 forward.

The above steps can be repeated as long as a movement is desired. Concluding, a group of multiple electro-magnetic actuators 5_1 to 5_5 along a transport path can be sequentially activated to move the container carrier 1 along the first transport path.

Since the electro-magnetic actuators 5 can be activated independently, it can be possible to independently and simultaneously move a plurality of different container carriers 1 along different paths, wherein self-evidently collisions have to be avoided.

Figure 9:
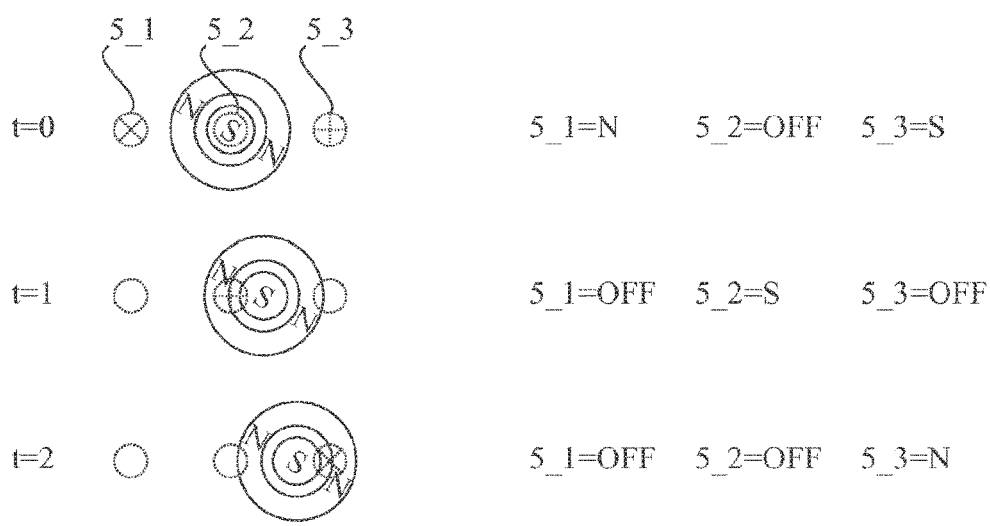
FIG. 9 illustrates movement of a container carrier and an activation order of corresponding electro-magnetic actuators according to a second embodiment of the present disclosure.

FIG. 9 shows a movement of a container carrier 1' and an activation order of corresponding electro-magnetic actuators 5_1 to 5_3 according to a second embodiment. FIG. 5 shows the container carrier 1' in more detail. In the shown embodiment, a movement of the container carrier 1' placed on a first electro-magnetic actuator 5_2 to an adjacent second electro-magnetic actuator 5_3 can comprise activating the first and the second electro-magnetic actuators 5_2 and 5_3 and a third electro-magnetic actuator 5_1 adjacent to the first electro-magnetic actuator 5_2 in a specific order and polarity. The electro-magnetic actuators 5_1 to 5_3 can be part of the same row or column and can be activated generating a south-pole (S) or a north-pole (N) pointing towards the container carrier F.

In a first step, at t=0, the second electro-magnetic actuator 5_3 can be activated such that a resulting pull-force regarding the second permanent magnet 7 having a ring shape can be generated and the third electro-magnetic actuator 5_1 can be activated such that a resulting push-force regarding the second permanent magnet 7 can be generated.

After the container carrier 1' reaches a first predetermined position at time t=1, what e.g. can be sensed by the container carrier sensing device, the second and third electro-magnetic actuators 5_1 and 5_3 can be deactivated and the first electro-magnetic actuator 5_2 can be activated such that a resulting pull-force regarding the second permanent magnet 7 can be generated and that a resulting push-force regarding the first permanent magnet 6 can be generated.

After the container carrier 1' reaches a second predetermined position at time t=2, the first and the third electro-magnetic actuators 5_1 and 5_2 can be deactivated and the second electro-magnetic actuator 5_3 can be activated such that a resulting pull-force regarding the second permanent magnet 7 can be generated.

In one embodiment, a movement between adjacent electro-magnetic actuators 5_2 and 5_3 can be performed in a sequence of three activation patterns regarding three adjacent electro-magnetic actuators 5_1 to 5_3. This can lead to a continuous uniform smooth movement with a high positioning accuracy.

Figure 10:
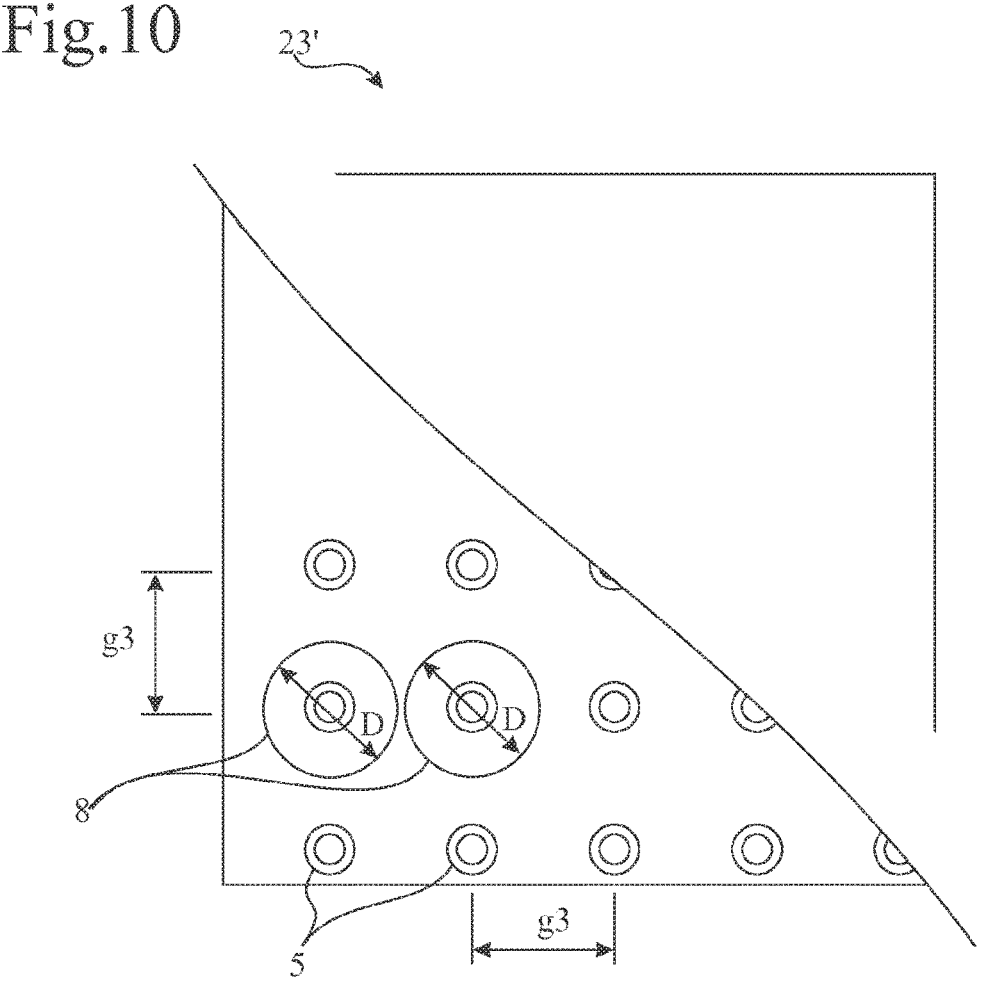
FIG. 10 illustrates a sub plane according to a further embodiment of the present disclosure.

FIG. 10 shows a further embodiment of a sub-plane 23'. According to this embodiment, the electro-magnetic actuators 5 can be arranged in rows and columns forming a grid having a single grid dimension g3. The distance between adjacent or consecutive electro-magnetic actuators 5 in each row and each column can be g3.

FIG. 10 depicts two exemplary container carriers each having a stand 8 with a circular cross section having a diameter D that can be approximately 1% to 20% smaller than the grid dimension g3. Due to this, two carriers moving on adjacent tracks can pass by each other without collision. On the other hand, the footprint can be large enough to provide a smooth transport without much tilting.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A laboratory sample distribution system, the laboratory sample distribution system comprising:
   a plurality of container carriers, wherein each container carrier carries a sample container;
   a transport plane to carry the container carriers; and
   a plurality of electro-magnetic actuators stationary arranged below the transport plane, wherein the electro-magnetic actuators move a container carrier on top of the transport plane by applying a magnetic force to said container carrier, wherein each container carrier comprises an arrangement of multiple permanent magnets and wherein the multiple permanent magnets comprise a first permanent magnet and a second permanent magnet having a ring shape surrounding the first permanent magnet.

2. The laboratory sample distribution system according to claim 1, wherein the electro-magnetic actuators comprise a ferromagnetic core having a center finger and four outer fingers, each of the fingers extending perpendicular to the transport plane.

3. The laboratory sample distribution system according to claim 1, wherein the multiple permanent magnets are made from hard ferromagnetic materials.

4. The laboratory sample distribution system according to claim 1, wherein the multiple permanent magnets are multipole permanent magnets.

5. The laboratory sample distribution system according to claim 1, wherein the container carrier has a cylindrical opening.

6. The laboratory sample distribution system according to claim 5, wherein the container carrier comprises flexible flat spring on a side wall on the cylindrical opening configured to affix the sample container within the container carrier.

7. A laboratory sample distribution system, the laboratory sample distribution system comprising:
   a plurality of container carriers, wherein each container carrier carries a sample container;
   a transport plane to carry the container carriers; and
   a plurality of electro-magnetic actuators stationary arranged below the transport plane, wherein the electro-magnetic actuators move a container carrier on top of the transport plane by applying a magnetic force to the container carrier and wherein each container carrier comprises a first permanent magnet arranged in a center of a stand of the container carrier and a second permanent magnet having a ring shape arranged in the stand surrounding the first permanent magnet.

8. The laboratory sample distribution system according to claim 7, wherein the second permanent magnet has a circular area having a diameter smaller than a distance between the axes of the electro-magnetic actuators.

9. The laboratory sample distribution system according to claim 7, wherein the first permanent magnet and the second permanent magnet have reverse polarity.

10. The laboratory sample distribution system according to claim 7, wherein a north pole of the first permanent magnet and a south pole of the second permanent magnet are directed towards the transport plane.

11. The laboratory sample distribution system according to claim 7, further comprises,
   a RFTD tag comprising a ring-shaped antenna.

12. The laboratory sample distribution system according to claim 11, wherein RFID tag stores a unique ID corresponding to the container carrier.

13. The laboratory sample distribution system according to claim 11, wherein the RFID tag is arranged in the stand between the first permanent magnet and the second permanent magnet.

14. The laboratory sample distribution system according to claim 7, wherein the electro-magnetic actuators comprise a ferromagnetic core having a center finger and four outer fingers, each of the fingers extending perpendicular to the transport plane.

15. A laboratory sample distribution system, the laboratory sample distribution system comprising:
   a plurality of container carriers, wherein each container carrier comprises at least one magnetically active device and carries a sample container;
   a transport plane to carry the container carriers; and
   a plurality of electro-magnetic actuators stationary arranged below the transport plane, wherein the electro-magnetic actuators move a container carrier on top of the transport plane by applying a magnetic force to said container carrier and wherein the electro-magnetic actuators comprise a ferromagnetic core having a center finger and four outer fingers, each of the fingers extending perpendicular to the transport plane, wherein only the center finger is surrounded by a coil.

16. The laboratory sample distribution system according to claim 15, wherein the coil is driven by an actuating current.

17. The laboratory sample distribution system according to claim 15, wherein each container carrier comprises an arrangement of multiple permanent magnets.

18. The laboratory sample distribution system according to claim 17, wherein the arrangement of multiple permanent magnets comprises a first permanent magnet and a second permanent magnet having a ring shape surrounding the first permanent magnet.

19. A laboratory sample distribution system, the laboratory sample distribution system comprising:
   a plurality of container carriers, wherein each container carrier comprises at least one magnetically active device and carries a sample container, wherein each container carrier comprises an arrangement of multiple permanent magnets, and wherein the arrangement of multiple permanent magnets comprises a first permanent magnet and a second permanent magnet having a ring shape surrounding the first permanent magnet;
   a transport plane to carry the container carriers; and
   a plurality of electro-magnetic actuators stationary arranged below the transport plane, wherein the electro-magnetic actuators move a container carrier on top of the transport plane by applying a magnetic force to said container carrier and wherein the electro-magnetic actuators comprise a ferromagnetic core having a center finger and four outer fingers, each of the fingers extending perpendicular to the transport plane.

* * * * *